United States Patent [19]

Ackermann et al.

[11] 4,228,084

[45] Oct. 14, 1980

[54] PROCESS FOR THE PRODUCTION OF GLYCIDYL METHACRYLATE

[75] Inventors: Rolf Ackermann; Heinz Kolb; Gerhard Morlock; Gerd Schreyer, all of Hanau, Fed. Rep. of Germany

[73] Assignee: Deutsche Gold- und Silber-Scheideanstalt vormals Roessler, Frankfurt, Fed. Rep. of Germany

[21] Appl. No.: 692,371

[22] Filed: Jun. 3, 1976

[30] Foreign Application Priority Data

Jun. 5, 1975 [DE] Fed. Rep. of Germany ....... 2525026

[51] Int. Cl.³ ............................................ C07D 301/00
[52] U.S. Cl. ................................................ 260/348.12
[58] Field of Search ....................... 260/348 A, 348.12

[56] References Cited

FOREIGN PATENT DOCUMENTS 2088971 1/1972 France .
47-38481 9/1972 Japan .
1374342 11/1974 United Kingdom .

OTHER PUBLICATIONS

Fieser et al., Reagents for Organic Synthesis, (1975), p. 553.
Chemical Abstracts, vol. 80, (1974), 47402d, abstracting Mori, K. et al., Synthesis, (1973), vol. 12, pp. 790–791.
Chemical Abstracts, vol. 83, (1975), 205778v, abstracting Japan. Kokai 75 52,013, 5/9/75.

Primary Examiner—Norma S. Milestone
Attorney, Agent, or Firm—Cushman, Darby & Cushman

[57] ABSTRACT

Glycidyl methacrylate is produced by transesterifying methyl methacrylate with glycidol in the presence of a polymerization inhibitor and a transesterification catalyst in which the catalyst is a salt of formula MeX where Me is an alkali metal ion and X is a cyanide, cyanate or thiocyanate ion.

9 Claims, No Drawings

PROCESS FOR THE PRODUCTION OF GLYCIDYL METHACRYLATE

The invention is directed to a process for the production of glycidyl methacrylate by transesterification of methyl methacrylate with glycidol in the presence of a polymerization inhibitor and a transesterification catalyst.

Glycidyl methacrylate is an interesting compound for polymer chemistry where it finds particular use in the coating sector, especially for the production of powder-coatings.

It is already known to produce glycidyl methacrylate by transesterification of methyl methacrylate with glycidol in the presence of a polymerization inhibitor and phosphine compounds as transesterification catalysts (Japanese published application No. 72/38421. Although the phosphine compounds dissolve homogeneously in the reaction mixture, however, in the known process the glycidol added is only reacted to a maximum of about 80 percent.

The object of the invention is the development of a process for the production of glycidyl methacrylate by transesterification of methyl methacrylate with glycidol in the presence of a polymerization inhibitor and a transesterification catalyst in which there is used as the transesterification catalyst at least one salt of the formula MeX in which Me is an alkali metal ion and X is a cyanide, cyanate or thiocyanate ion. Examples of such catalysts are sodium cyanide, potassium cyanide, sodium cyanate, potassium cyanate, sodium thiocyanate, potassium thiocyanate and lithium cyanide.

The alkali metal cyanides, alkali metal cyanates and alkali metal thiocyanates used as transesterification catalysts according to the invention are suitably added in the amount of 1 millimole to 500 millimoles and preferably in the amount of 5 millimoles to 100 millimoles per mole of glycidol.

Especially preferred is the use of potassium cyanide, potassium cyanate or potassium thiocyanate. However, the use of potassium cyanide is most preferred.

The salts used as transesterification catalysts according to the invention are scarcely soluble in methyl methacrylate. In an unexpected manner, however, in heterogeneous phase they catalyze the transesterification up to a very high reaction of the glycidol added and thereby make possible the production of higher yields. The transesterification proceeds substantially quicker than possible side reactions, as the addition of the hydroxyl group of the glycidol to the double bond, the addition of cyanide, cyanate or thiocyanate to the double bond or the addition of cyanide, cyanate or thiocyanate to the epoxide grouping. However, it is particularly surprising that neither the glycidol employed nor the glycidyl methacrylate formed polymerizes or that polymerization occurs not even to a small extent. The process of the invention yields therethrough especially high yields of glycidyl methacrylate, mostly above 90%, based on the glycidol employed.

The greatest part of the transesterification catalysts used according to the invention is easily separated off from the reaction mixture, for example, by simple filtration. The residue remaining does not further disturb the working up and remains in the distillation residues.

As starting materials there are employed methyl methacrylate and glycide (glycidol, 2,3-epoxypropanol-1). The process of the invention is carried out in the presence of at least one of the known inhibitors for radical polymerizations. Among the known substances, there can be used, for example, hydroquinone, hydroquinone monomethyl ether, tert. butyl pyrocatechol; other monohydric and polyhydric phenols such as 2,4-dimethyl-6-tert.butyl phenol, for example; quinones, e.g., benzoquinone or quinone; aminophenols, e.g., p-aminophenol; aromatic amines, such as diphenylamine, phenyl-$\beta$-naphthylamine, N,N'-diphenyl-benzidine; or quinone dyestuffs such as methylene blue. They are suitably used in an amount between about 100 and about 1000 ppm based on the total weight of the reactants.

The transesterification is preferably so carried out that the methyl methacrylate, which is used in a molar ratio of between about 2:1 to about 10:1, preferably between 4:1 to 10:1 based on the glycidol employed, together with the glycidol and at least one inhibitor is first dewatered azeotropically in a suitably dimensioned reactor with an effective column.

The glycidol can also be present together with the methyl methacrylate and the inhibitor without dewatering, or the glycidol can be fed into the methyl methacrylate during the transesterification reaction. Then the alkali metal cyanide, alkali metal cyanate or alkali metal thiocyanate is added and a methyl methacrylate-methanol azeotrope withdrawn over the column at a pressure in the inside of the reaction vessel between 760 Torr and 200 Torr. The boiling point of the methyl methacrylate-methanol azeotrope is 65° C. for example at a pressure of 760 Torr. The azeotrope has a methanol content of 84.5%. At a pressure of 200 Torr the azeotrope temperature is 34.6° C. and the azeotrope has a content of 80% methanol. By changing the pressure in the inside of the reaction vessel between these two values there can be established any intermediate azeotrope temperature. The reaction temperature according to the pressure thereby is so regulated that there is always maintained a strong reflux in the column. It is normally about 20° to 40° C. above the azeotrope temperature. After about 2 to 5 hours of removing distillate, the transesterification is ended. After cooling the reaction vessel, it is filtered off from the catalyst and the filter residue washed with a little methyl methacrylate. The glycidyl methacrylate is recovered from the filtrate by distillation in a known manner.

Unless otherwise indicated, all parts and percentages are by weight.

The following examples further explain the process of the invention.

EXAMPLE 1

There were present in a 1 liter three necked flask, 500 grams (5 moles) of methyl methacrylate and 74 grams (1 mole) of glycidol as well as, as polymerization inhibitor, 0.5 grams of 2,4-dimethyl-6-tert.butyl phenol. Then there was added 0.55 grams (8.5 millimoles) of potassium cyanide and the mixture heated to 70° to 80° C. There were immediately distilled off over a 20 cm. packed column (Raschig rings, 6 mm diameter) at a pressure of 200 Torr, the methanol formed together with methyl methacrylate at a reflux ratio of 3:1. Air was introduced via a capillary during the reaction. After 2 hours reaction time, the glycidol transformation was 98.0% and the glycidyl methacrylate yield 94.7%. Both values were determined gas chromatographically. After filtration of the contents of the flask, the residual methyl methacrylate and unreacted glycidol were distilled off via a thin layer evaporator under vacuum. The resultant crude glycidyl methacrylate was again distilled at 10 Torr (B.P.$_{10}$; 74°–75° C.). The glycidyl methacrylate was obtained as a colorless liquid (Purity >>97%) in a yield of 122 grams (86% of theory).

EXAMPLE 2

As described in Example 1, there were reacted 74 grams (1 mole) of glycidol with 500 grams (5 moles) of methyl methacrylate under addition of 0.5 grams of 2,4-dimethyl-6-tert.butylphenol as inhibitor and 0.55 grams of potassium cyanate (6.8 millimoles) added as catalyst. After 3 hours, the glycidol reaction amounted to 95% and the glycidyl methacrylate yield to 91.6%. The yield of pure product was 82%.

EXAMPLE 3

As described in Example 1, 74 grams (1 mole) of glycidol was reacted with 500 grams (5 moles) of methyl methacrylate with addition of 0.5 grams of 2,4-dimethyl-6-tert.butyl phenol as inhibitor and 1.0 gram of potassium thiocyanate (10.3 millimoles) as catalyst. After three hours the glycidol reaction was 95.7% and the glycidyl methacrylate yield was 92.5%.

EXAMPLE 4

400 grams (4 moles) of methyl methacrylate, 4.74 (73 millimoles) grams of KCN and 0.118 gram (250 ppm) of N,N'-diphenylbenzidine in a 1 liter round bottom flask were heated to 90° to 100° C. with passage of air therethrough. Within one further hour there were charged 74 grams (1 mole) of glycidol and thereby the methyl methacrylate-methanol azeotrope withdrawn from the column head via a 1 meter Vigreux column at about 65° C. After 2.5 hours, the reaction was ended, which was shown by the increase of the head temperature. The sump was filtered free of potassium cyanide and washed with a little methyl methacrylate. After distilling off the methyl methacrylate there remained behind 132 grams of glycidyl methacrylate (93% yield). The product can be worked up by distillation for further purification (B.P.$_{10}$, 71°–75° C.).

EXAMPLE 5

There were present in a 1 liter round bottomed flask 400 grams (4 moles) of methyl methacrylate, 0.118 grams (250 ppm) of hydroquinone methyl ester and 74 grams (1 mole) of glycidol and the product dewatered azeotropically while leading air therethrough. After cooling of the contents of the flask to 60° to 70° C. there were added 0.325 grams (5 millimoles) KCN and the mixture heated with the passage through of air to an inner temperature of 90° to 100° C. The methyl methacrylate-methanol azeotrope was withdrawn over a 1 meter Vigreux column at a head temperature of 65° C. After 3 hours the reaction was ended. The sump was filtered away from the potassium cyanide and washed with a little methyl methacrylate. After distilling off of the methyl methacrylate there remained behind a yield of 140 grams ≙ (98.5%) of glycidyl methacrylate. The product can be worked up by distillation for further purification.

The process can comprise, consist essentially of, or consist of the steps set forth using the materials set forth.

What is claimed is:

1. A process for producing glycidyl methacrylate by transesterifying methyl methacrylate with glycidol in the presence of a polymerization inhibitor and a transesterification catalyst, the improvement comprising employing as the catalyst a salt of the formula MeX where Me is an alkali metal ion and X is a cyanide, cyanate or thiocyanate.

2. The process of claim 1, wherein Me is sodium or potassium.

3. The process of claim 2, wherein the salt is used in an amount of 1 millimole to 500 millimoles per mole of glycidol.

4. The process of claim 3, wherein the salt is used in an amount of 5 millimoles to 100 millimoles per mole of gylcidol.

5. The process of claim 3 wherein the salt is a potassium salt.

6. The process of claim 3, wherein the salt is potassium cyanide.

7. The process of claim 3, wherein the pressure is between 700 Torr and 200 Torr and the methyl methacrylate-methanol azeotrope formed is removed at a temperature ranging from 65° C. to 34.6° C.

8. The process of claim 7, wherein the salt is potassium cyanide.

9. The process of claim 1, wherein the salt is a potassium salt.

* * * * *